US008866894B2

(12) United States Patent
Wong et al.

(10) Patent No.: US 8,866,894 B2
(45) Date of Patent: Oct. 21, 2014

(54) METHOD FOR REAL-TIME VISUALIZATION OF CARIES CONDITION

(75) Inventors: Victor C. Wong, Rochester, NY (US); Gary M. Spinelli, Hilton, NY (US); Peter D. Burns, Fairport, NY (US); Paul O. McLaughlin, Rochester, NY (US); Jean Marc Inglese, Bussy Saint Georges (FR)

(73) Assignee: Carestream Health, Inc., Rochester, NY (US)

( * ) Notice: Subject to any disclaimer, the term of this patent is extended or adjusted under 35 U.S.C. 154(b) by 1275 days.

(21) Appl. No.: 12/017,400

(22) Filed: Jan. 22, 2008

(65) Prior Publication Data

US 2009/0185712 A1 Jul. 23, 2009

(51) Int. Cl.
 *G06K 9/00* (2006.01)
 *A61B 5/00* (2006.01)
 *G06T 7/00* (2006.01)

(52) U.S. Cl.
 CPC ..... *G06T 7/0012* (2013.01); *G06T 2207/30036* (2013.01); *A61B 5/0088* (2013.01); *G06T 2207/10016* (2013.01); *G06T 2207/20141* (2013.01); *G06T 7/0081* (2013.01)
 USPC ............... 348/77; 348/66; 382/128; 382/130; 382/162; 433/25; 433/29

(58) Field of Classification Search
 CPC .. A61B 5/0088; G06T 7/0081; G06T 7/0012; G06T 2207/30036; G06T 2207/10016; G06T 2207/20141
 USPC ......... 348/77, 66; 382/128, 130, 162; 433/25, 433/29
 See application file for complete search history.

(56) References Cited

U.S. PATENT DOCUMENTS

| 4,290,433 A | 9/1981 | Alfano |
| 4,479,499 A | 10/1984 | Alfano |
| 4,515,476 A | 5/1985 | Ingmar |
| 5,321,501 A | 6/1994 | Swanson et al. |
| 5,570,182 A | 10/1996 | Nathel et al. |
| 6,122,103 A | 9/2000 | Perkins et al. |
| 6,179,611 B1 | 1/2001 | Everett et al. |
| 6,231,338 B1 | 5/2001 | de Josselin de Jong et al. |
| 6,522,407 B2 | 2/2003 | Everett et al. |

(Continued)

FOREIGN PATENT DOCUMENTS

| JP | 2004-237081 | 8/2004 |
| JP | 2004-344260 | 12/2004 |
| JP | 2006-527615 | 12/2006 |
| WO | WO 03/005892 | 1/2003 |

OTHER PUBLICATIONS

Kevin Carter et al., "Automated quantification of dental plaque accumulation using digital imaging," Journal of Dentistry, Nov. 1, 2004, vol. 32, No. 8, pp. 623-628, XP004596983.
Iain A. Pretty, "Caries detection and diagnosis: Novel technologies," Journal of Dentistry, vol. 34, No. 10, Nov. 1, 2006, pp. 727-739, XP025066288.

(Continued)

*Primary Examiner* — Kenneth Coulter (57) ABSTRACT

A method for displaying live video of a tooth identifies a tooth tissue region in a viewable image frame obtained from a video stream and processes pixel data within the tooth tissue region to identify a suspected caries site. Intensity values for pixels that correspond to the suspected caries site are modified and a highlighted viewable image frame is formed as a combination of the modified intensity values corresponding to the suspected caries site and other pixel values in the viewable image frame. The highlighted viewable image frame is displayed in video form.

19 Claims, 10 Drawing Sheets

(56) References Cited

U.S. PATENT DOCUMENTS

| | | | |
|---|---|---|---|
| 7,596,253 | B2 * | 9/2009 | Wong et al. .................. 382/128 |
| 7,702,139 | B2 | 4/2010 | Liang et al. |
| 8,270,689 | B2 | 9/2012 | Liang et al. |
| 2004/0023184 | A1 | 2/2004 | de Josselin de Jong et al. |
| 2004/0202356 | A1 | 10/2004 | Stookey et al. |
| 2004/0240716 | A1 | 12/2004 | de Josselin de Jong et al. |
| 2005/0003323 | A1 | 1/2005 | Katsuda et al. |
| 2005/0024646 | A1 | 2/2005 | Quadling et al. |
| 2005/0244794 | A1 | 11/2005 | Kemp et al. |
| 2006/0239526 | A1 | 10/2006 | Jonusauskas et al. |
| 2007/0099148 | A1 | 5/2007 | Wong et al. |

OTHER PUBLICATIONS

Extended European Search Report dated Sep. 7, 2010, from the European Patent Office re: Application No. 08 021 737.5, 7 pages.

Fried et al., "Imaging caries lesions and lesion progression with polarization sensitive optical coherence tomography", Journal of Biomedical Optics 7(4), 618-627 (Oct. 2002).

Quantitative Light-induced Fluoroescence, (QLF) Clinical System from Inspektor Research Systems BV, Amsterdam, The Netherlands. 7 pages. (Jan. 15, 2008).

Brochure: KaVo DIAGNOdent Laser Caries Detection Aid from KaVo Dental Corporation, Lake Zurich, Illinois. 6 pages (Brochure undated.), entered into case on Jan. 22, 2008.

Brochure: KaVo DIAGNOdent Laser Caries Detection Aid from KaVo Dental Corporation, Lake Zurich, Illinois. 2 pages, Oct. 10, 2012.

Diagnodent Laser Caries Detection Aid from KaVo Dental Corporation, Lake Zurich, Illinois.

Wong et al., "Method and Apparatus for Detection of Caries," U.S. Appl. No. 11/262,869, filed Oct. 31, 2005.

Liang et al., "Apparatus for Caries Detection," U.S. Appl. No. 11/530,987, filed Sep. 12, 2006.

Liang et al., "Apparatus for Caries Detection," U.S. Appl. No. 11/549,208, filed Oct. 13, 2006.

* cited by examiner

METHOD FOR REAL-TIME VISUALIZATION OF CARIES CONDITION

FIELD OF THE INVENTION

This invention generally relates to methods and apparatus for dental imaging and more particularly relates to apparatus and methods for identifying and highlighting caries in displayed real-time video images that are obtained from a patient's teeth.

BACKGROUND OF THE INVENTION

In spite of improvements in detection, treatment, and prevention techniques, dental caries remain a widely prevalent condition affecting people of all age groups. If not properly and promptly treated, caries can lead to permanent tooth damage and even to loss of teeth.

Traditional methods for caries detection include visual examination and tactile probing with a sharp dental explorer device, often assisted by radiographic (x-ray) imaging. Detection using these methods can be somewhat subjective, varying in accuracy due to many factors, including practitioner expertise, location of the infected site, extent of infection, viewing conditions, accuracy and sensitivity of x-ray equipment and processing, and other factors. There are also hazards associated with conventional detection techniques, including the risk of damaging weakened teeth and spreading infection with tactile methods as well as exposure to x-ray radiation. By the time caries are evident under visual and tactile examination, the disease is generally in an advanced stage, requiring a filling and, if not timely treated, possibly leading to tooth loss.

In response to the need for improved caries detection methods, there has been considerable interest in improved imaging techniques that do not employ x-rays. In particular, it has been shown that certain optical responses differ between sound and carious tooth regions. Difference in light scattering properties causes reflectance of light from the illuminated tooth area to be at measurably different levels for normal versus carious areas. This effect can be used to help identify tooth regions with early caries, which tend to appear brighter than surrounding sound structures in images captured by reflectance imaging devices, such as an intraoral camera.

Another optical method that has been employed for caries detection is based on tooth fluorescence, emitted when teeth are illuminated with high intensity ultraviolet-blue light. This technique operates on the principle that sound, healthy tooth enamel yields a higher, predominately green fluorescence intensity under excitation from some wavelengths than does de-mineralized enamel that has been damaged by caries infection. The strong correlation between mineral loss and loss of green fluorescence for ultraviolet-blue light excitation is then used to identify and assess carious areas of the tooth. A different relationship has been found for red fluorescence, a region of the spectrum for which bacteria and bacterial by-products in carious regions fluoresce more pronouncedly than do healthy areas.

Among commercialized products for dental imaging using green fluorescence behavior is the Quantitative Light Fluorescence (QLF) Clinical System from Inspektor Research Systems BV, Amsterdam, The Netherlands. Using a different approach, the Diagnodent Laser Caries Detection Aid from KaVo Dental Corporation, Lake Zurich, Ill., detects caries activity by monitoring the intensity of red fluorescence of bacterial by-products under illumination from red light.

In the related U.S. patent applications cited earlier, another optical technique known as fluorescence imaging with reflectance enhancement (FIRE) has been described for caries detection. In the FIRE method described in these applications, both reflectance and fluorescence imaging effects are combined, enabling caries to be detected with higher contrast from surrounding sound tooth structures.

One problem that is common to existing dental imaging systems relates to the delay period between the time that the tooth is initially being screened and the image of the tooth is obtained and the time a possible caries condition is identified or reported to the dentist or technician. With existing systems, tooth screening (during which the images are obtained) and caries detection (during which the images are processed and analyzed to identify carious regions) are carried out as two separate steps. In practice, at an appropriate point during screening, a still image capture is first obtained from the tooth in response to an operator instruction. Then, in a subsequent step, the image data are processed and analyzed for carious conditions to provide the clinician with a processed image (possibly also accompanied by a report) indicating caries information, such as apparent location, size, and severity, for example. This caries information is available only after the conclusion of the tooth screening step and only after image processing/analysis steps are completed.

When the caries information becomes available at this later time after screening, the dentist often needs to go back and re-examine the imaged tooth in order to look more closely at the reported problem area. This delay is inconvenient and lengthens the duration of the examination session. It can be appreciated that there would be an advantage to an apparatus that would provide more immediate feedback to the examining practitioner, so that problem areas can be identified and examined more closely at the time of screening. However, this advantage is not available with conventional systems, due to factors such as the difficulty of detection, the intensive computation requirements needed for many existing detection methods, and the amount of image data that is required for each tooth.

In spite of some advancements, an acknowledged problem with real-time detection for existing dental imaging systems relates to the difficulty of identifying caries in teeth images without extensive image processing or absent a highly skilled practitioner who is familiar with this specialized equipment. Systems such as the QLF system described earlier may show real-time fluorescence images, but these displayed images are generally only of value to the experienced clinician who is trained in interpreting the displayed image from tooth fluorescence in order to identify a caries area. In general, caries detection from tooth images, whether using white light or fluorescence images, requires a relatively high level of expertise from the practitioner. Auto-detection by computer-aided image analysis can eliminate the expertise requirement. However, because current auto-detection algorithms usually involve time-consuming image processing; they are not suitable for real time identification of caries.

It can be appreciated that there would be advantages to a method of image processing that can quickly identify carious areas from teeth images to provide immediate feedback of information suggestive of carious conditions. Such a method would allow auto-detection of caries in real time that would be useful even for the novice or relatively untrained user.

SUMMARY OF THE INVENTION

An object of the present invention is to address the need for improved screening and diagnostic workflow for dental imaging. With this object in mind, the present invention provides a method for displaying live video of a tooth comprising:

a) identifying a tooth tissue region in a viewable image frame obtained from a video stream;
b) processing pixel data within the tooth tissue region to identify a suspected caries site;
c) modifying intensity values for pixels that correspond to the suspected caries site;
d) forming a highlighted viewable image frame as a combination of the modified intensity values corresponding to the suspected caries site and other pixel values in the viewable image frame; and
e) displaying the highlighted viewable image frame in video form.

A feature of the present invention is that an image processing method for caries detection is provided that is substantially faster than known methods, so that suspected carious areas can be identified without extensive and time-consuming image processing operations.

An advantage of the present invention is that it can provide real time identification of likely sites of dental caries, an identification that can take place as the tooth is being screened.

Another advantage of the present invention is that it provides clear visual indication of caries sites that would be useful for the novice or relatively untrained user.

These and other aspects, objects, features and advantages of the present invention will be more clearly understood and appreciated from a review of the following detailed description of the preferred embodiments and appended claims, and by reference to the accompanying drawings.

BRIEF DESCRIPTION OF THE DRAWINGS

While the specification concludes with claims particularly pointing out and distinctly claiming the subject matter of the present invention, it is believed that the invention will be better understood from the following description when taken in conjunction with the accompanying drawings, wherein:

DETAILED DESCRIPTION OF THE INVENTION

Reference is made to commonly-assigned copending (a) U.S. Patent Application Publication No. 2007/0099148 entitled "Method And Apparatus For Detection Of Caries" by Wong et al, U.S. patent application Ser. No. 11/262,869 filed Oct. 31, 2005 issued as U.S. Pat. No. 7,596,253; (b) U.S. patent application Ser. No. 11/530,987 now U.S. Pat. No. 8,270,689 entitled "Apparatus for Caries Detection" by Liang et al filed Sep. 12, 2006, U.S. Patent Application Publication No. 2008/0063998; and (c) U.S. patent application Ser. No. 11/549,208 entitled "Apparatus for Caries Detection" by Liang et al filed Oct. 13, 2006, U.S. Patent Application Publication No. 2008/0090198, issued as U.S. Pat. No. 7,702,139. The disclosures of these copending applications are incorporated by reference into the present application It is to be understood that elements not specifically shown or described may take various forms well known to those skilled in the art.

Methods of the present invention address the need for real-time caries detection information about each tooth at the same time the tooth is being screened by an intra-oral imaging apparatus. To do this, the present invention takes advantage of both reflectance and fluorescence effects from caries sites and modifies frames in the video stream to indicate suspect sites.

In the context of this disclosure, the term "fluorescence" is broadly used to include image data generated either by fluorescence itself or by processing fluorescence data in combination with reflectance data, such as in FIRE imaging described earlier.

In the context of this disclosure, the term "diagnostic" is used in a general sense, to include data, procedures or techniques that help to indicate a possible problem area, thus directing the attention of a dental practitioner to it. Thus, the term "diagnostic" is intended to encompass systems and procedures, and information obtained thereby, used for dental screening as well as for detailed assessment of caries with a high degree of accuracy.

The term "screening" is used herein to describe that portion of the routine initial examination procedure in which a practitioner moves an intra-oral probe from one tooth to the next in sequence and positions the probe to obtain a video or still image at each tooth, for at least some number of teeth. Conventionally, a display monitor is used to help manipulate the probe for imaging. As the practitioner moves the probe through the mouth during screening, a displayed video image from the probe helps the practitioner to guide the probe position and to navigate from tooth to tooth. When the operator has the probe in an appropriate position, one or more still images may be captured by controlling a shutter on the probe itself or on the accompanying imaging workstation equipment.

In conventional practice, the captured image data are then uploaded to a host processor for analysis using the image processing algorithms that perform caries detection/diagnostic image analysis, such as those using fluorescence, reflectance, or some other feature or effect recorded in the captured image. Once processing has been completed, the processed image may be displayed with indication of carious areas; a report of some type on suspected caries areas may also be provided when using conventional workflow for diagnostic dental imaging.

Of particular interest for the present invention is the capability for rapid processing of either or both reflectance and fluorescence information in order to provide caries detection information as "real-time" feedback during the screening activity itself. The apparatus and methods of the present invention thus identify and visually highlight suspected caries sites for the practitioner at the time of screening the tooth surface, at video rates. By alerting the operator to a probable caries site at the time of screening, the method of the present invention helps to direct operator attention to the site for more comprehensive diagnostic assessment of that area. As a result, the need to return to a tooth in a follow-up imaging session is less likely and the overall workflow for caries detection imaging can be made more efficient and effective.

In the context of the present disclosure, the term "real-time" is used to describe the relative speed of the image processing and display operations for caries site identification and highlighting as comparable to the video refresh rate that applies during screening. For the present invention, then, caries site detection can be considered as real-time processing if some amount of processed detection information about the condition of the tooth that is currently at the probe position can be made available to the operator as the tooth is still being screened. As a coarse indication of threshold processing rates required, a video image refresh rate of at least about 10 frames per second or faster would satisfy the need for real-time detection. This can be distinguished from the conventional dental imaging workflow for caries detection that requires an initial step of obtaining a still image capture during tooth screening, followed by subsequent steps of image processing of the still image for caries detection analysis. Because of the time this more complex processing/analysis takes in conventional apparatus, caries detection results are not available to the operator until after an additional and significant amount of time, well after initial screening is completed. The typical delay period may be a few seconds or longer, depending on how extensive the processing/analysis is. The real-time imaging feature of embodiments of the present invention helps the operator by identifying and highlighting suspected problem areas so that particular care and action can be taken by the operator for those areas during screening. Subsequent still image captures at these suspected locations could be made to provide more image data to support further, more comprehensive diagnosis.

Figure 1:
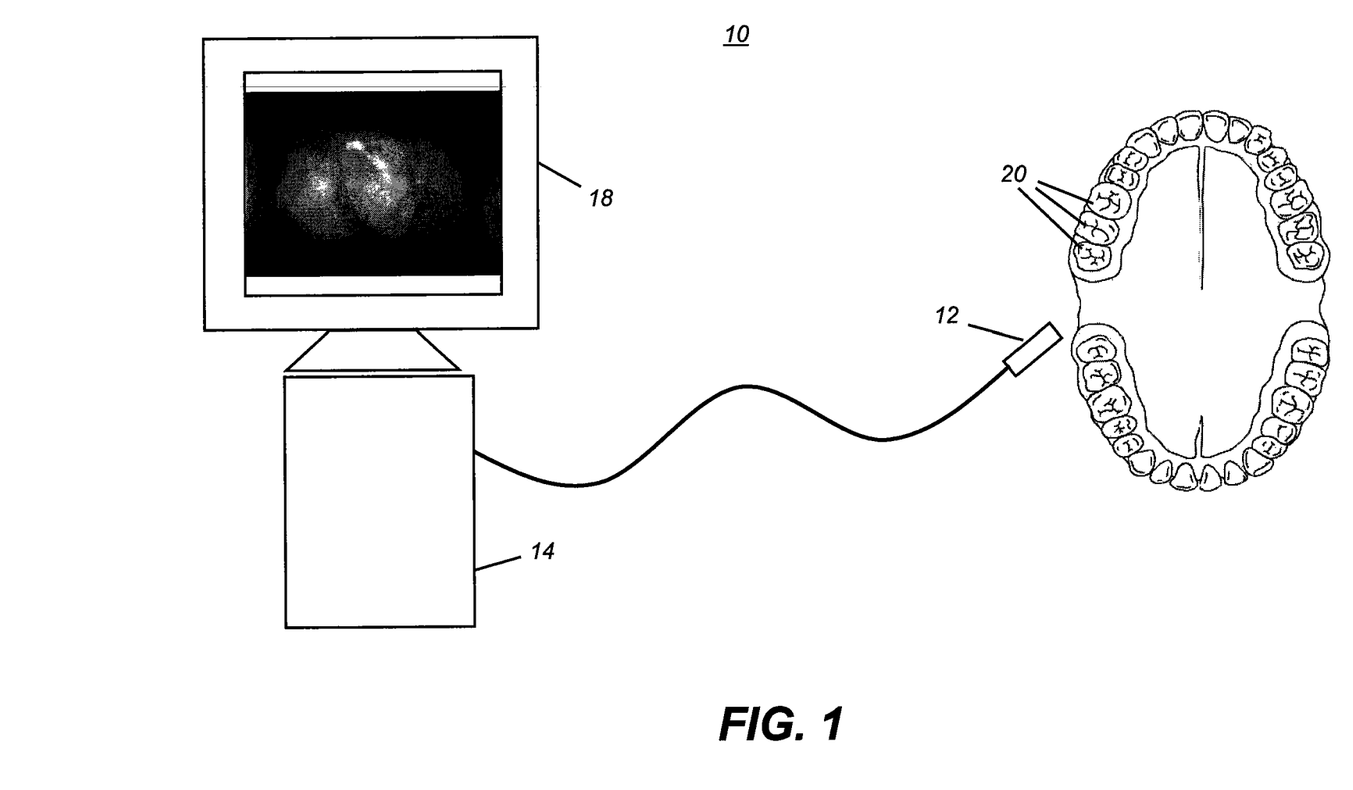
FIG. 1 is a schematic diagram of an apparatus for dental imaging according to one embodiment.

The schematic block diagram of FIG. 1 shows a caries detection system 10 according to one embodiment. A probe 12 is guided along teeth 20 by an operator to conduct a tooth screening session. Probe 12 itself contains one or more light sources, an imaging sensor or camera (monochrome or color) that is capable of both still and video imaging, and support optics for imaging. Probe 12 can be capable of forming an image using reflectance (such as an intraoral camera) or fluorescence, or both (such as a FIRE system). Probe 12 connects, either through a cable or through wireless interface, to a control logic processor 14. Control logic processor 14 provides the image processing logic for processing data from probe 12. For the video signal, control logic processor 14 performs image formation processing on the raw image frames from the sensor (typically consisting of operations such as sensor color filter array interpolation, color correction, and color rendering, for example), then converts them to viewable image frames for video display. In one embodiment, control logic processor 14 also executes the needed logic for FIRE processing of the image data. Control logic processor 14 could alternately execute other image processing logic, including auto-detection processing that identifies caries features by analyzing fluorescence image data, reflectance image data, or some combination of fluorescence and reflectance image data, and then highlighting or exaggerating the suspected caries sites in some way. A display 18 provides the operator with a real-time video view from probe 12 as the teeth are being screened.

Figure 2A:
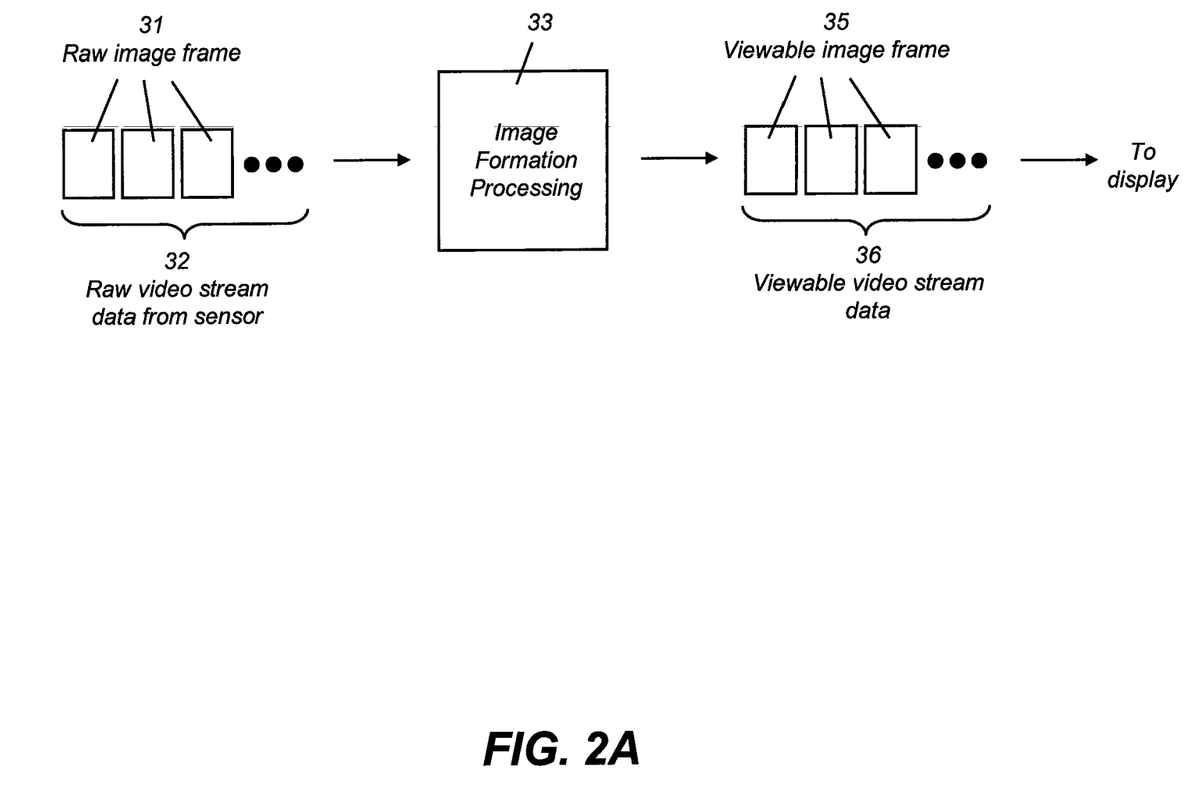
FIG. 2A shows the video image processing and display path during a tooth screening operation in a conventional intraoral imaging system.
Figure 2B:
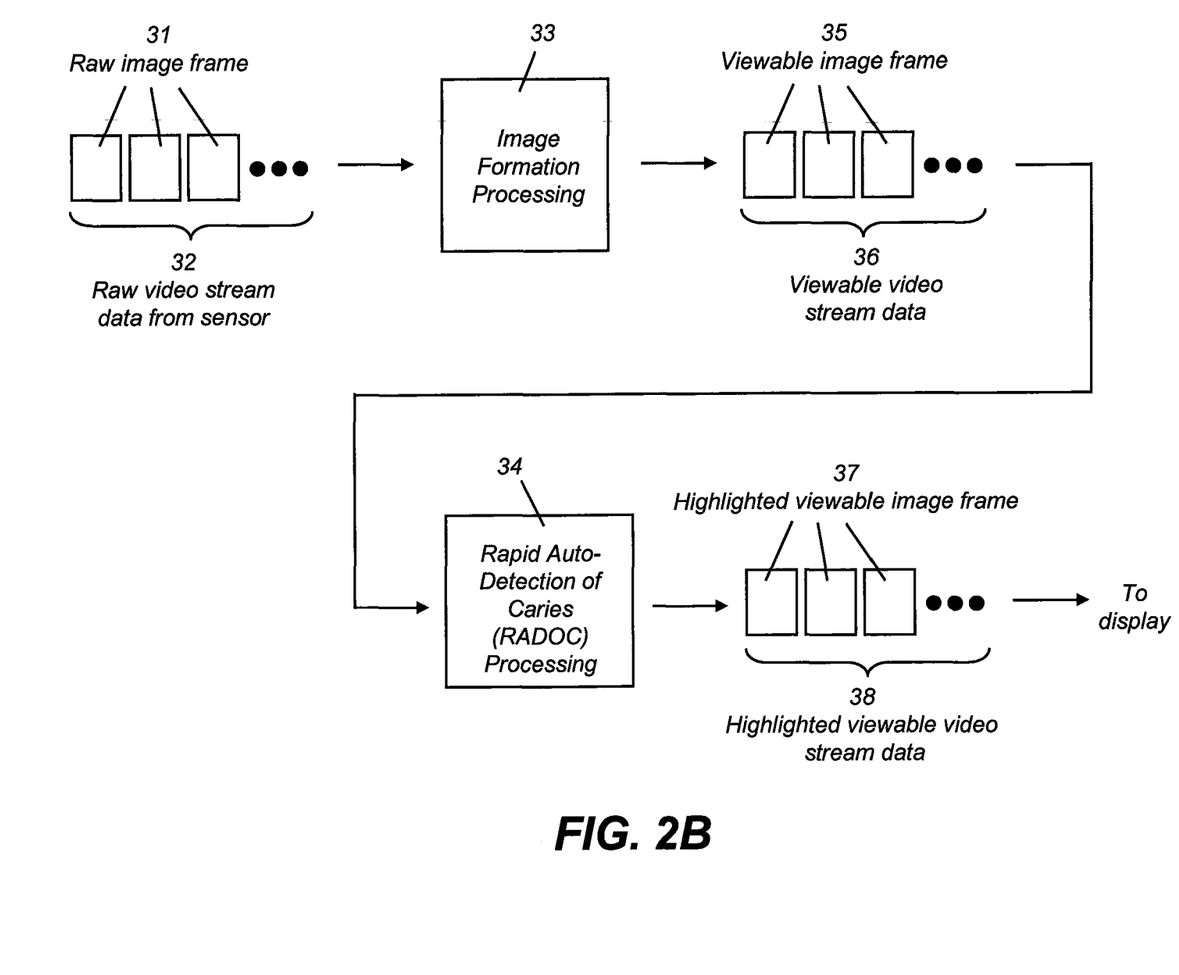
FIG. 2B shows the video image processing and display path during a tooth screening operation in an intraoral imaging system according to the present invention.

FIGS. 2A and 2B show how the present invention is distinguished from conventional methods for dental image processing and display during a tooth screening procedure. Referring first to FIG. 2A, in a conventional intraoral imaging system such as the QLF system described earlier, raw video stream data 32 from the sensor of intra-oral probe 12 are directly converted by control logic processor 14 (FIG. 1) into viewable video stream data 36 for viewing on display 18. An image formation processing step 33 is performed on the raw image frames 31 of the raw video stream data 32 by control logic processor 14. This processing includes standard video image data processing functions such as interpolation and color correction, for example. The output is viewable video stream data 36 which provide viewable image frames 35.

Now turning to FIG. 2B, the image processing and display path of embodiments of the present invention is shown. These embodiments provide detection and visualization of caries sites in real time as the teeth are being screened. After performing image formation processing step 33, control logic processor 14 performs additional processing, termed Rapid Auto-Detection Of Caries (RADOC) processing 34, on each viewable image frame 35 for identifying and highlighting of caries sites. The resulting highlighted viewable video stream data 38 contain highlighted viewable image frames 37, which are viewable image frames showing suspected caries sites highlighted on the video display that is viewed by the operator performing the screening procedure. Importantly, RADOC processing 34 can execute quickly enough to support real time viewing of the highlighted viewable video stream data 38 on display 18. A description follows of how RADOC processing 34 can be implemented for real-time caries detection and visualization in different embodiments.

RADOC Processing

Figure 3:
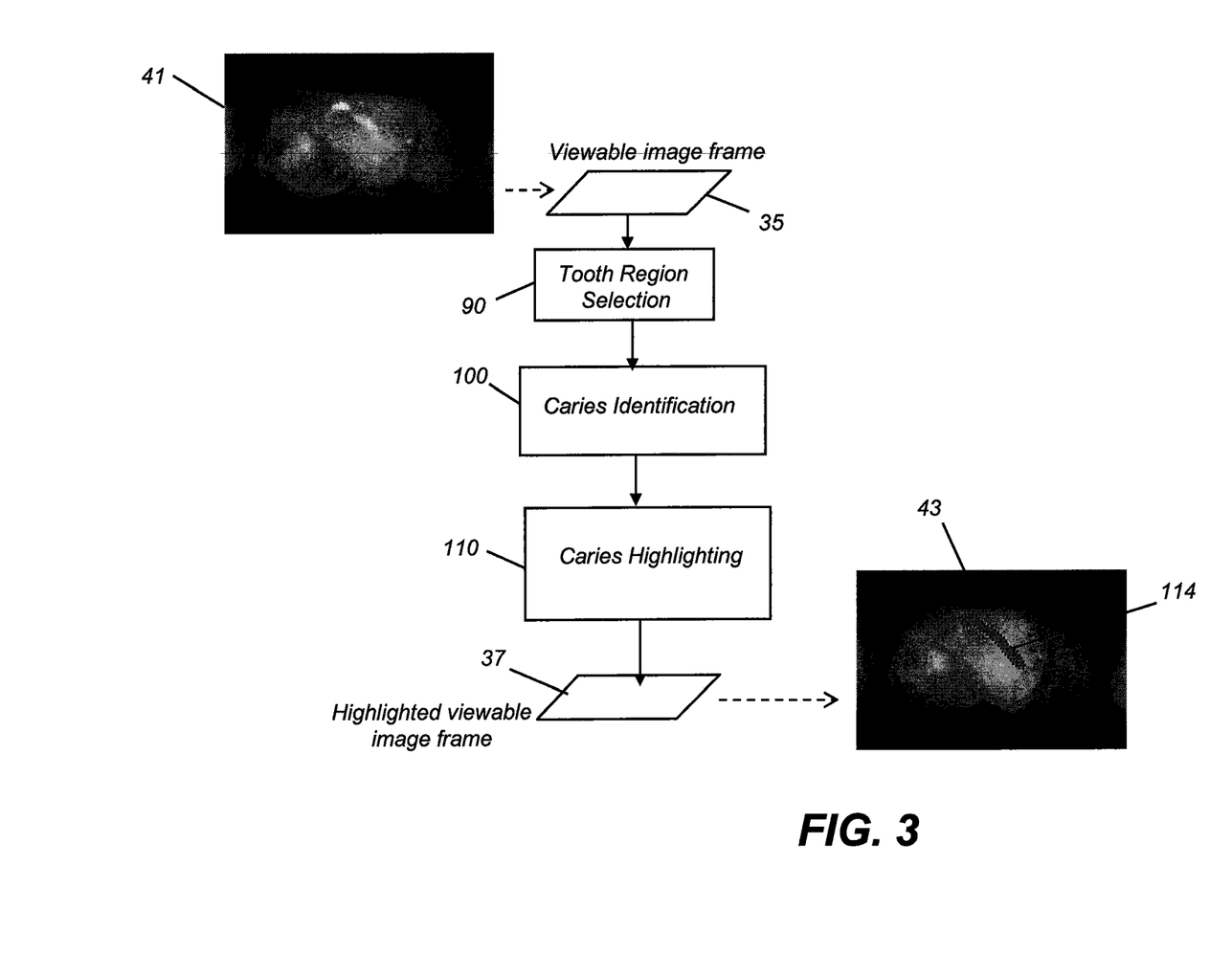
FIG. 3 is a logic flow diagram showing a sequence of steps for implementing rapid auto-detection of caries (RADOC) processing according to one embodiment.

The logic flow diagram of FIG. 3 shows a sequence of steps that are used for implementing RADOC processing 34 as was described with respect to FIG. 2B. An outline of the steps is given now; and the implementation of each step will be discussed in greater detail in the different embodiments below.

As caries detection system 10 is used to screen each tooth 20, light is captured by the camera or sensor on probe 12 to form viewable image frames 35 at a rapid video rate. Viewable image frame 35 typically has red, green, and blue (R, G, and B) color planes. A color plane of a viewable image frame 35 of a tooth is shown in image 41 as an example. A tooth region selection step 90 is first performed on at least one of the color planes to select and segment the tooth region from surrounding tissue and background. This is accomplished, for example, using segmentation techniques familiar to those skilled in the diagnostic imaging arts. For live video, this can mean detecting multiple regions, as probe 12 (FIG. 1) is moved from one tooth to the next.

Next, a caries identification step 100 is executed on the selected image data, wherein pixels indicating suspected caries sites are identified. Then, in a caries highlighting step 110, the identified pixels are modified, highlighted in some way in order to create an exaggeration effect in viewable image frame 35.

Pixel modification in caries highlighting step 110 can be carried out in a number of ways. In one embodiment, pixel values in one color plane are mapped to higher intensity values, as described subsequently. In other embodiments, more complex image processing is performed, using techniques such as adding false-color effects, such as highlighting using synthetic colors or displaying other colors not expected to be sensed within the mouth. Outlining or shading can alternately be used. Alternative forms of pixel modification could also be utilized for more clearly highlighting the detected caries sites.

At the conclusion of the sequence shown in the logic flow diagram of FIG. 3, highlighted viewable image frame 37 is generated. Highlighted viewable image frame 37 shows the image of the tooth with caries infection site(s) identified and exaggerated. The highlighted viewable image frame 37 corresponding to the unmodified video frame of image 41 is shown in an image 43. In this example, the detected caries location is highlighted by darkening and providing an outline 114 of a caries site. Highlighted viewable image frame 37 is then provided as part of highlighted viewable video stream data 38 for video viewing on display 18 (FIG. 1).

RADOC Embodiments Using Reflectance

As noted earlier, tooth regions that are subject to early caries exhibit somewhat higher reflectance than other regions. These regions can appear brighter (or whiter) than sound tooth structures and are sometimes termed "white spots". Regions having advanced caries, however, tend to lose reflectivity and appear to be darker than surrounding structures. In a digital image representation, the brighter spots (that is, sites indicating early caries) have higher pixel values, and the darker regions (indicating advanced caries) have lower pixel values, as compared to the pixel values of the sound tooth structures. Both the high reflectance of early caries and the low reflectance of advanced caries allow these conditions to be distinguished from sound tooth condition using white light or other color light.

As described with reference to FIG. 2B, RADOC processing 34 must operate with sufficient speed for modifying the image data stream at video rates. The method of the present invention performs this processing using digital data operations that can be performed quickly on the large volume of image data that is obtained from the viewable image frames 35.

Figure 4:
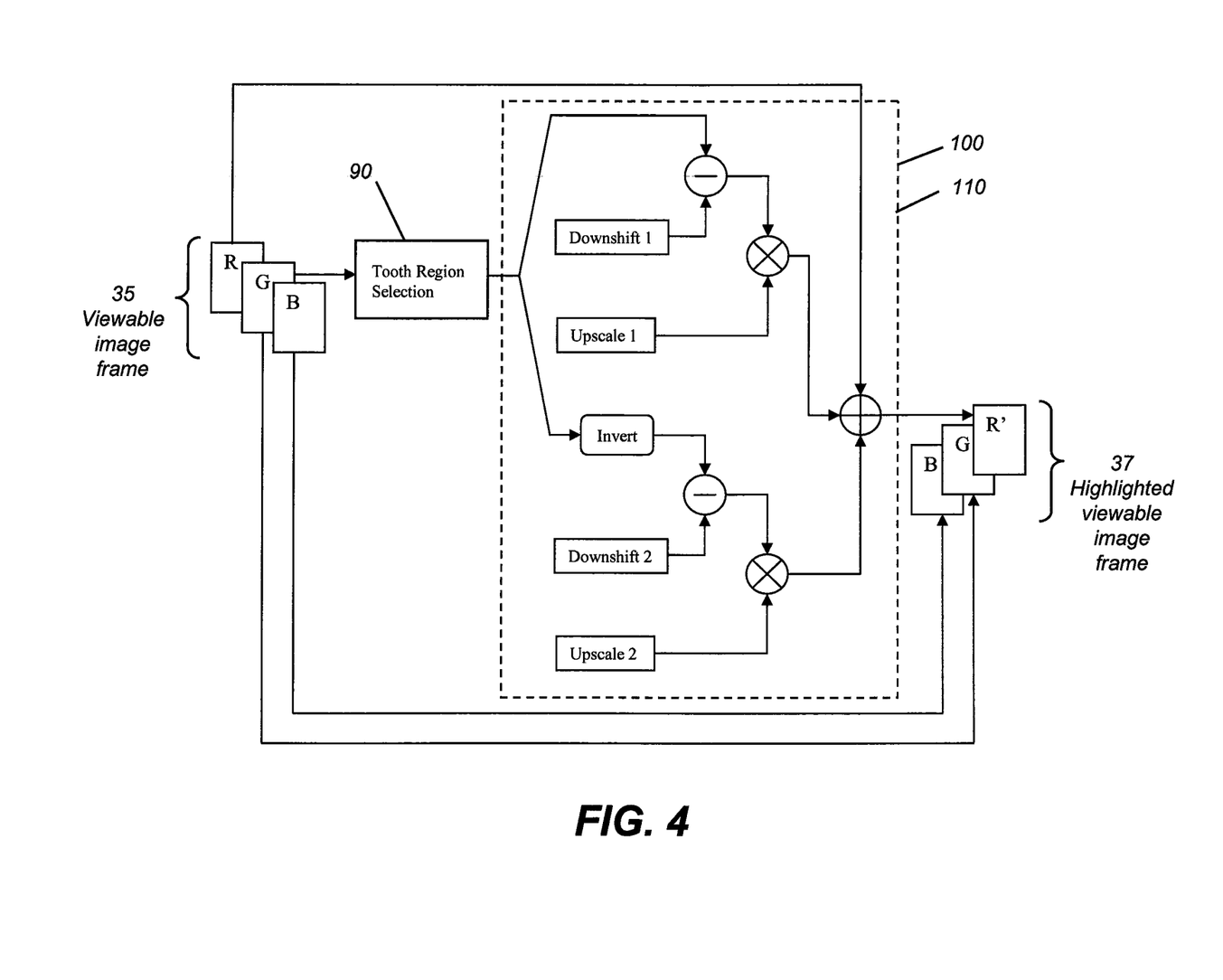
FIG. 4 is the block diagram for implementing RADOC processing using reflectance image frames according to one embodiment.

When caries detection system 10 is used in the reflectance mode, viewable image frames 35 are simply reflectance images of the tooth, such as images obtained under illumination by white light or some other color light. FIG. 4 shows a block diagram for one embodiment of RADOC processing using reflectance image frames. Combined procedures for caries identification step 100 and caries highlighting step 110 are shown in dashed outline. The red, green, and blue (R, G, and B) color planes of a particular viewable image frame 35 are shown as the input. For carrying out a tooth region selection step 90, a single image plane may be used, indicated as the Green (G) image plane in the example of FIG. 4. (Either the Red or Blue plane or a gray scale image plane could alternately be used.). The Green plane has advantages, since this color plane tends to include the luminance data to a higher degree than other color planes. Tooth region selection step 90 is first performed on this single color plane in order to segment and select the tooth tissue from surrounding tissue and background. This is accomplished by a segmentation technique. As has been noted, segmentation techniques are familiar to those skilled in the imaging arts.

Figure 5:
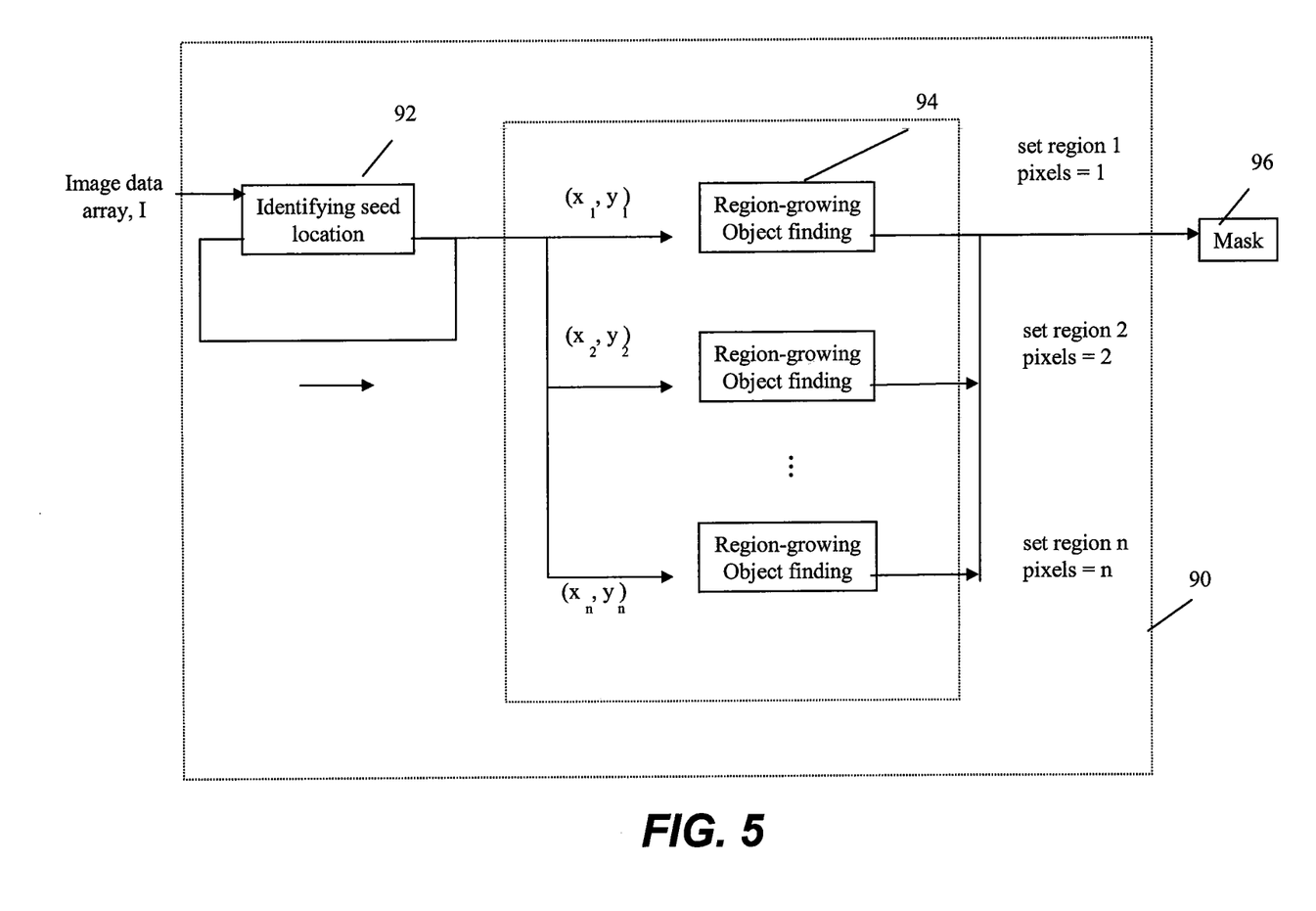
FIG. 5 is a logic flow diagram of a segmentation technique for selecting tooth region in an intraoral image.

FIG. 5 shows an example of the processing sequence of tooth region selection step 90 that can be applied to an image data array I. The first step is an identifying seed location step 92. Identifying seed location step 92 identifies a seed pixel or pixel area I(i,j) based on characteristics of the intended region of interest. For example, image aspects such as color or brightness can be used for identifying a seed pixel that lies within the tooth tissue in the obtained image data. For cases when multiple regions are to be identified, multiple (x,y) seed locations are selected. For each seed location, a region-growing segmentation operation 94 can then be performed. In one method, each of the immediately surrounding pixels is examined to identify which pixels have values within a tolerance value of the seed pixel, I(i,j). This is done repeatedly for each identified pixel to form regions. Regions are groups of contiguous pixels identified by their value. The set of identified pixels contiguous to a seed constitute a single region. For each region, the corresponding locations are set to suitable values in a mask 96 of the same size as the image array. For example, region 1 might be identified as having a value equal to 1. The result is a mask array with regions identified. This method can be used to set apart the tooth tissue region in the image, either by selecting the pixels in the tooth structure, or by selecting the pixels in the surrounding gum tissue and background.

Returning to FIG. 4, after tooth region selection step 90, two separate sets of processing operations are then executed on the selected image data. One set of operations, shown toward the upper portion of the diagram, identifies and amplifies pixels in early caries regions, using a subtraction operation followed by a multiplication operation, as follows:

(i) In the subtraction operation, all pixel values are subtracted by a fixed constant amount, Downshift 1. Pixels with values smaller than Downshift 1 are clipped to zero values, so that only pixels with values greater than Downshift 1 still have non-zero values after the subtraction. Effectively, this leaves only the demineralized, white spots on the tooth as areas with non-zero pixel values.

(ii) In the ensuing multiplication operation, pixels are multiplied by a multiplicative factor, Upscale 1. The scaling amplifies the brightness values of only the non-zero pixels; it thus creates an amplification effect on the intensity of early caries sites in the image. Although scalar multiplication is used in this embodiment, some other form of pixel value enhancement could be used as an alternative to produce similar kind of amplification effects.

Another set of operations executed on the selected tooth region image data, shown toward the lower portion of the diagram in FIG. 4, identifies and amplifies pixels in regions having caries in its more advanced stages. This set of operations consists of inversion, followed by subtraction, then followed by multiplication, as follows:

(iii) Inversion is performed to invert the values of all pixels in the selected tooth region, (iv) Subtraction is then executed, which subtracts all pixel values by a fixed amount, Downshift 2. Pixels with values smaller than Downshift 2 are clipped to zero values, so that only advanced caries regions have non-zero pixel values.

(v) Multiplication is then executed, amplifying the intensity of the advanced caries regions by the factor Upscale 2.

The optimal values of Downshift 1, Downshift 2, Upscale 1, and Upscale 2 are device dependent and are empirically determined beforehand through a calibration procedure for the caries detection system 10.

At the conclusion of the sequence shown in FIG. 4, results of the two sets of operations described above (steps i and ii; steps iii, iv, v) provide enhanced pixel values that are localized to sites that have a high likelihood of caries infection. These enhanced pixel values are then used to modify the input image data in order to form the highlighted viewable image frame 37 that displays (FIG. 3). In the embodiment shown in FIG. 4, enhanced pixel values from each of the sets of operations are added to the Red color plane of viewable image frame 35. The composite image of highlighted viewable image frame 37 contains the same Green and Blue color planes as viewable image frame 35, but has its Red color plane modified by the enhanced pixel values indicative of early and advanced caries data, labeled as R' in the figure. This composite image of highlighted viewable image frame 37 shows the caries sites detected and highlighted in red color. It can be appreciated that although the Red color plane of viewable image frame 35 is used for the image addition in the example of FIG. 4, any one of the color planes can be used for the same purpose.

Figure 6:
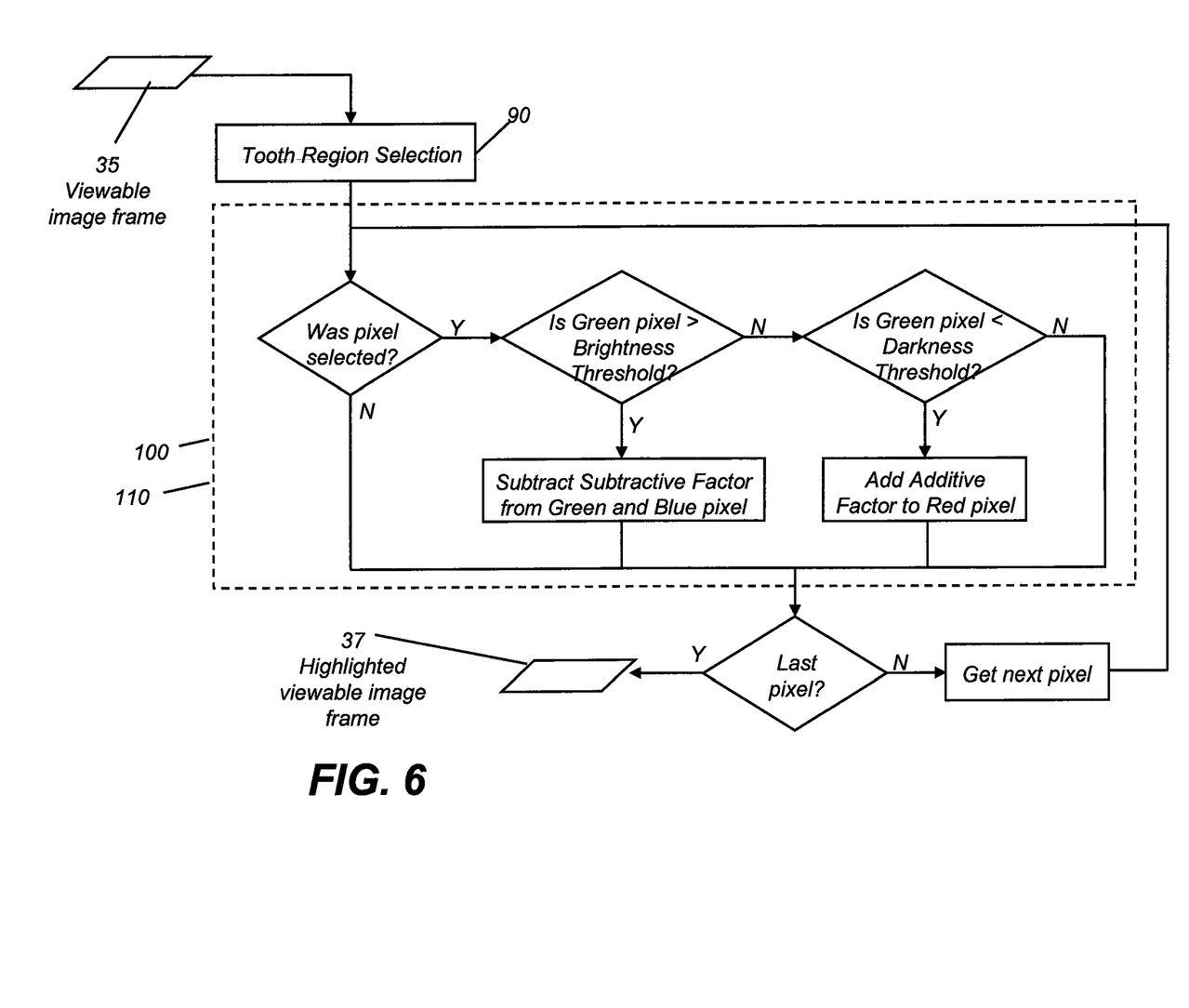
FIG. 6 is a logic flow diagram for implementing RADOC processing using reflectance image frames according to an alternative embodiment.

FIG. 6 shows the logic flow diagram for an alternative embodiment of RADOC processing using reflectance image frames, again provided as tristimulus color data in individual planes. Tooth region selection step 90 is first performed on viewable image frame 35 as was described with the FIG. 4 embodiment. A segmentation algorithm similar to that described in tooth region selection step 90 shown in FIG. 5 can be used to select the tooth region from surrounding tissue and background. Combined procedures for caries identification step 100 and caries highlighting step 110 are shown inside dashed outline. For every pixel site that is selected, the Green pixel value is separately compared against two threshold values: Brightness Threshold and Darkness Threshold. (Red or Blue pixels could alternatively be used for the value checks.) The following processing is performed:
 (i) If the Green pixel value is greater than Brightness Threshold, early caries is detected, and the image pixel is modified to have a red appearance by subtracting a Subtractive Factor from the Green and Blue pixel values.
 (ii) If the Green pixel is less than Darkness Threshold, advanced caries is detected, and the image pixel is modified to have an exaggerated red color by adding an Additive Factor to the Red pixel.

Image pixels that fall between the two threshold values are assumed to be in the healthy regions indicating sound tooth tissue and are left unmodified. Then the next image pixel is checked, and the loop is repeated until all image pixels have been checked. The result is highlighted viewable image frame 37, in which detected caries sites are highlighted in red color; and early and advanced caries are distinguished by different shades of red color.

For the FIG. 6 embodiment, the optimal values of Brightness Threshold and Darkness Threshold are device dependent and can be empirically determined beforehand through a calibration procedure for caries detection system 10. Values for Subtractive Factor and Additive Factor are also predetermined; the larger their values, the stronger the highlight effects at the detected carious pixels.

The above-described methods can be used with any type of oral imaging system that can obtain a reflectance or white light image from the tooth during an examination session. For optimal results, imaging probe 12 should be configured to minimize specular reflection, such as by the use of crossed polarized light, as discussed in the related U.S. patent applications cited earlier.

RADOC Embodiments Using Fluorescence

A similar sequence to the logic used in FIG. 2 can also be applied for a tooth imaging apparatus that obtains fluorescence image data. It may be advantageous to use fluorescence to generate caries highlights, since tooth regions having caries in any of its stages, early as well as advanced, appear as dark regions in the fluorescence image. Caries sites can thus be detected in simpler processing steps, as will be seen below. Highlighting can then be performed on the displayed fluorescence image or on a white-light image.

Figure 7:
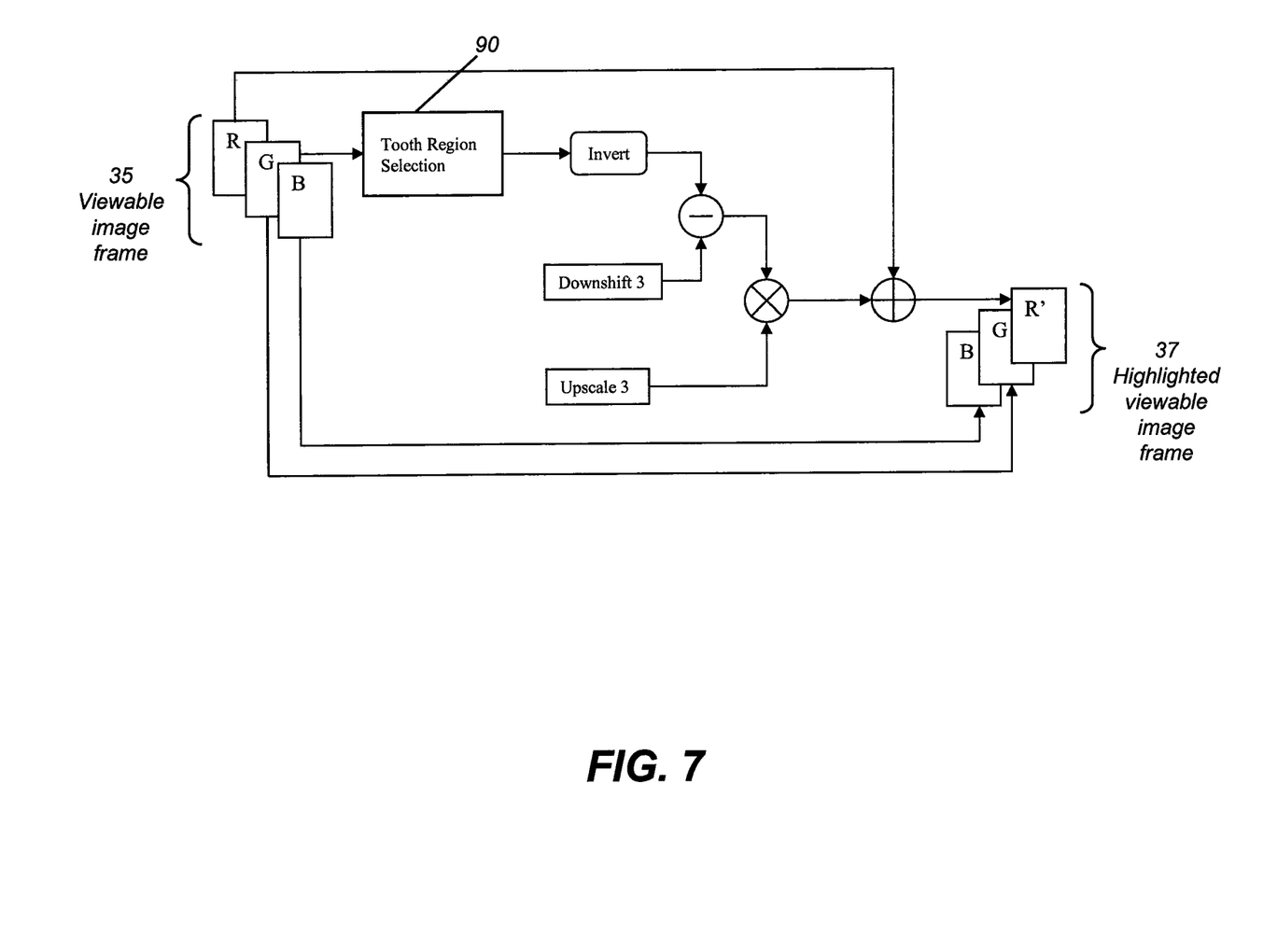
FIG. 7 is a logic flow diagram for implementing RADOC processing using fluorescence image frames according to one embodiment.

The logic flow diagram of FIG. 7 shows the steps for identifying and highlighting caries data using fluorescence. In green fluorescence imaging, pixel values in Red and Blue color planes are very low and are close to the background values. The Green color plane, on the other hand, contributes most to the intensity of viewable image frame 35. In FIG. 7, viewable image frame 35 is a fluorescence image. A tooth region selection step 90 is first performed on the Green color plane of viewable image frame 35 to select the tooth region from surrounding tissue and background. This is accomplished by a segmentation technique similar to what is shown in FIG. 5. For identifying and amplifying pixels in regions with caries, sequential operations of inversion, subtraction, and multiplication are carried out on the selected image data, as follows:
 (i) Inversion is performed to invert the values of all pixels in the selected tooth region.
 (ii) Subtraction is then executed, which subtracts all pixel values by a fixed amount, Downshift 3. Pixels with values smaller than Downshift 3 are clipped to zero values, so that only caries regions have non-zero pixel values.
 (iii) Multiplication is then executed, amplifying the intensity of the caries regions by the factor Upscale 3.

Optimal values of Downshift 3 and Upscale 3 are device dependent and are empirically determined beforehand through a calibration procedure for the caries detection system 10. Result of the multiplication is added to the image data of the Red color plane of viewable image frame 35. The composite image thus contains the same Green and Blue color planes as viewable image frame 35, but with the Red color plane modified by the caries data, labeled as R' in the figure. This composite image is highlighted viewable image frame 37, which shows the caries sites that have been detected and highlighted in red color in the fluorescence image. Using the example sequence of FIG. 7, although the Red color plane of viewable image frame 35 is used for the image addition, any one of the color planes can be used for the same purpose.

Figure 8:
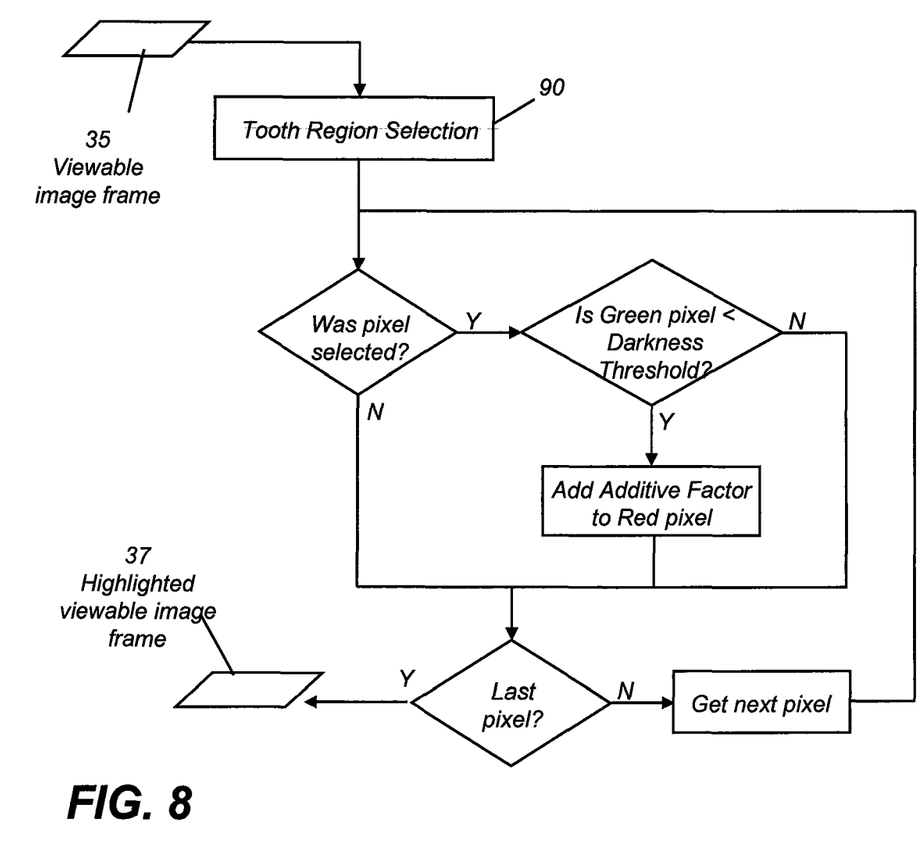
FIG. 8 is a logic flow diagram for implementing RADOC processing using fluorescence image frames according to an alternative embodiment.

FIG. 8 shows the logic flow diagram for an alternative embodiment of RADOC processing using fluorescence. Tooth region selection step 90 is first performed on the fluorescence viewable image frame 35 in the same way as in previously described embodiments. A segmentation algorithm similar to that described in FIG. 4 can be used to select the tooth tissue from surrounding tissue and background. For every pixel site that is selected, the Green pixel value is compared against the Darkness Threshold value. A suitable value of Darkness Threshold is device dependent and can be empirically determined beforehand through a calibration procedure for caries detection system 10. A decision process follows. If the Green pixel value is less than a Darkness Threshold, caries is detected, and the image pixel is modified to have an exaggerated red color by adding Additive Factor to the Red pixel. Image pixels that do not satisfy the criterion are in the healthy regions and are left unmodified. Then the next image pixel is checked, and the loop is repeated until all image pixels have been checked. The result is highlighted viewable image frame 37, in which detected caries sites are highlighted in red color in the fluorescence image.

The Additive Factor is predetermined; the larger its value, the stronger the highlight effects at the detected carious pixels. Additive Factor could have a range of values. Larger values could be used for the addition operation for larger differences between the Green pixel value and Darkness Threshold, and vice versa. In this way, caries at different stages are highlighted with different shades of red color.

Figure 9:
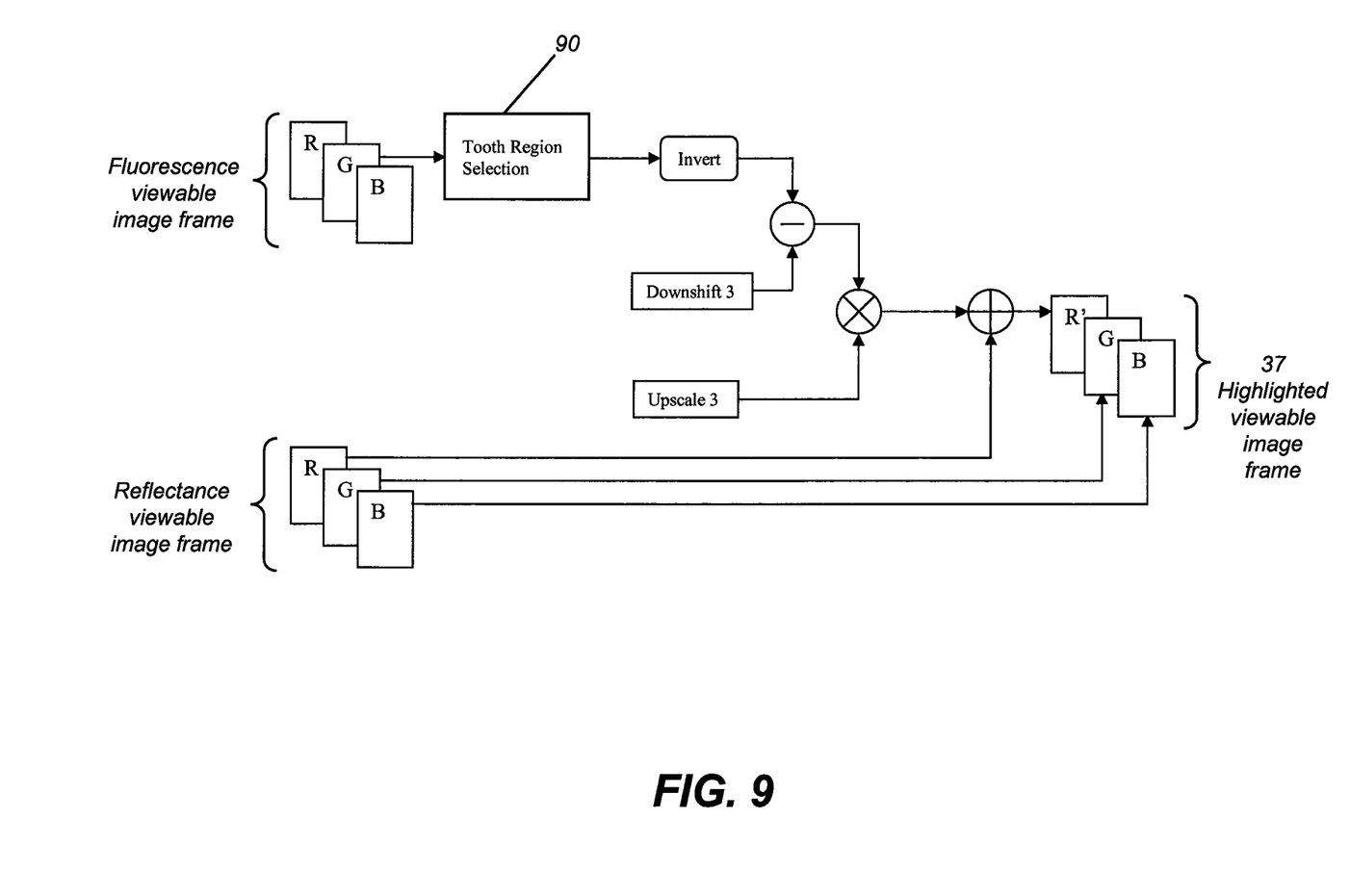
FIG. 9 is a logic flow diagram for RADOC processing that identifies caries from fluorescence image frames and highlights carious regions in reflectance image frames.

Referring now to FIG. 9, as an alternative embodiment to that shown in FIG. 8, both reflectance viewable image frames and fluorescence viewable image frames can be captured at almost the same time (from alternating white light illumination and blue-violet light illumination, for example), close enough in sequence so that there is one-to-one correspondence between the pixels in the two viewable image frames. Then, while the operations for caries identification are carried out on the fluorescence viewable image frame (as in FIG. 8), pixels detected with carious conditions are actually modified in the reflectance viewable image frame. (Inversion, downshift subtraction, and multiplicative scaling processes can follow the pattern described earlier with reference to FIGS. 4 and 7.) The resulting highlighted viewable image frame 37 for display is a white light or reflectance image frame with caries highlighted. This alternative implementation can be similarly applied to the embodiment in FIG. 8.

In practice, real-time caries detection and reporting using fluorescence can require more complex imaging apparatus and higher-speed computing power than detection using reflectance. In spite of these difficulties, embodiments of the present invention using real-time fluorescence detection and caries reporting may be advantaged with some types of dental imaging apparatus, even if the displayed image refresh rate may not be as fast as with reflectance imaging.

The exemplary image processing methods described with reference to FIGS. 4-9 can be modified in any of a number of ways and still provide identification and highlighting of caries sites that can be accessed by the operator in real-time video mode. Given this visual feedback during the screening session, the operator can more carefully examine areas where caries in some form has been detected.

Certainly, the information needed for highlighting problem areas, obtained according to embodiments of the present invention, can be used to improve overall quality of dental imaging and of the overall oral examination. Using the method of the present invention, the total amount of data that must be stored and processed for more thorough dental imaging can be dramatically reduced. Instead of painstakingly obtaining an image from each tooth, the operator can be more selective, confidently moving from one tooth to the next, pausing to capture image data for further processing only where the visual feedback provided by the present invention indicates a likely need for more detailed information. Moreover, the operator can screen different tooth surfaces more efficiently in order to more accurately detect a likely caries condition.

Advantageously for speed, the image processing sequence can be executed very rapidly, allowing quick update of display 18 (FIG. 1). Software for executing suitable algorithms for this method can be configured to operate on various processor types, or even to execute on logic circuitry that is contained within probe 12 itself. Additional processing steps could be used to increase reporting speed, such as using sub-sampling, for example. Some amount of sub-sampling could be used to perform caries site detection at reduced resolution. However, if done excessively, sub-sampling could tend to compromise the quality of the feedback information that is provided.

The invention has been described in detail with particular reference to certain preferred embodiments thereof, but it will be understood that variations and modifications can be effected within the scope of the invention as described above, and as noted in the appended claims, by a person of ordinary skill in the art without departing from the scope of the invention. For example, color planes other than those described in the examples of FIGS. 4-9 could be used, either for obtaining data for assessment or for reporting problem areas. Results from early or more advanced caries could be combined, as described with reference to FIGS. 4 and 9, or could be separately displayed. Display 18 (FIG. 1) could show multiple versions of the reflectance and/or fluorescence image, such as with and without highlighting of caries sites or other problem areas. Enhanced display capabilities can alternately be coupled with audible indicators such as emitted tones that could prompt the operator to attend more carefully to areas having suspected caries sites.

Thus, what is provided is an apparatus and method for rapid identification and highlighting of caries conditions in displayed images obtained in real time from a patient's teeth.

PARTS LIST

10. Caries detection system
12. Probe
14. Control logic processor
18. Display
20. Tooth
31. Raw image frame
32. Raw video stream data
33. Image formation processing step
34. Rapid Auto-Detection of Caries (RADOC) processing
35. Viewable image frame
36. Viewable video stream data
37. Highlighted viewable image frame
38. Highlighted viewable video stream data
41. Image
43. Image
90. Tooth region selection step
92. Identifying seed location step
94. Region-growing segmentation operation
96. Mask
100. Caries identification step
110. Caries highlighting step
114. Outline

The invention claimed is:

1. A method for displaying live video of a caries condition of a tooth, the method comprising:
   identifying a tooth tissue region of a single color plane in a single viewable image frame obtained from a video image stream of the tooth;
   processing pixel data within the tooth tissue region of the single color plane to identify pixels that correspond to a suspected caries site, wherein processing the pixel data comprises inverting pixel values of the pixels that correspond to the suspected caries site;
   modifying intensity values for the pixels that correspond to the suspected caries site;
   forming a single highlighted viewable image frame by adding the modified intensity values for the pixels to other pixel values in the single viewable image frame; and
   displaying the live video including the single highlighted viewable image frame.

2. The method of claim 1 wherein processing the pixel data comprises subtracting a fixed value from the pixel values that correspond to the suspected caries site.

3. The method of claim 1 wherein modifying the intensity values generates a synthetic color not normally found within human mouth tissue.

4. The method of claim 1 wherein processing the pixel data comprises comparing the pixel values of the pixels that correspond to the suspected caries site against one or more threshold values.

5. The method of claim 1 wherein processing the pixel data comprises comparing the pixel values from the single color plane against one or more threshold values and wherein modifying the intensity values comprises modifying pixel values from a second color plane.

6. The method of claim 1, further comprising sub-sampling the pixel data within the viewable imaging frame prior to processing the pixel data to identify the pixels that correspond to the suspected caries site.

7. The method of claim 1 wherein processing the pixel data further comprises multiplying the inverted pixel values by a constant value.

8. The method of claim 1 wherein processing the pixel data further comprises subtracting or adding a constant value from the pixel values in the viewable imaging frame.

9. The method of claim 1 wherein steps of processing the pixel data, modifying the intensity values, and forming the highlighted viewable image comprise processing each pixel value within the tooth tissue region by testing the pixel value against a darkness threshold and, if the pixel value is less than the darkness threshold, adding a first value to the pixel value in at least one color plane, forming the highlighted viewable image thereby.

10. The method of claim 9, further comprising testing the pixel values against a brightness threshold and, if the pixel values exceed the brightness threshold, subtracting the first value from the pixel values in at least a second color plane.

11. The method of claim 1, wherein inverting the pixel values further comprises inverting a first set of the pixel values that corresponds to a first suspected caries site, and wherein processing the pixel data further comprises:
  subtracting a first amount from the first set of pixel values after the first set of pixel values has been inverted; and
  multiplying the first set of pixel values by a second amount after the first amount has been subtracted.

12. The method of claim 11, wherein processing the pixel data further comprises:
  subtracting a third amount from a second set of the pixel values, the second set of pixel values corresponding to a second suspected caries site; and
  multiplying the second set of pixel values by a fourth amount after the third amount has been subtracted.

13. A method for displaying live video of a caries condition of a tooth, the method comprising:
  obtaining a viewable image frame from a video image stream of the tooth;
  processing a first color plane of the viewable image frame by:
    identifying a tooth tissue region within a first color plane of the viewable image frame, and
    processing selected pixels within the tooth tissue region of the first color plane to generate pixel values that are indicative of one or more caries sites, wherein processing the pixel data comprises inverting the pixel values;
  modifying a second color plane of the viewable image frame by combining the pixel values that are indicative of the one or more caries sites with corresponding pixel values of the second color plane; and
  re-combining the first and second color planes, and any additional color planes, to provide a highlighted viewable image frame for video display.

14. The method of claim 13 wherein processing the first color plane comprises obtaining a fluorescence image from the viewable image frame.

15. The method of claim 14 wherein the fluorescence image is generated from combined processing of reflectance and fluorescence image captures.

16. The method of claim 13 wherein processing the first color plane comprises obtaining a reflectance image from the viewable image frame.

17. A method for displaying live video of a caries condition of a tooth, the method comprising:
  obtaining a reflectance viewable image frame from a reflectance video stream of the tooth;
  obtaining a fluorescence viewable image frame from a fluorescence video stream of the tooth;
  processing a color plane of the fluorescence viewable image frame by:
    identifying a tooth tissue region within the color plane of the fluorescence viewable image frame, and
    processing selected pixels within the tooth tissue region of the color plane to generate pixel values that are indicative of one or more caries sites,
  wherein processing the pixel data comprises inverting the pixel values;
  modifying a color plane of the reflectance viewable image frame by combining the pixel values that are indicative of the one or more caries sites with corresponding pixel values of the color plane from the reflectance viewable image frame to form a highlighted viewable image frame; and
  displaying the highlighted viewable image frame.

18. The method of claim 17 wherein the reflectance viewable image frame is obtained with white light illumination.

19. The method of claim 17 wherein the fluorescence image frame is generated from combined processing of reflectance and fluorescence image captures.

\* \* \* \* \*